United States Patent
Barrett et al.

(10) Patent No.: US 6,622,038 B2
(45) Date of Patent: Sep. 16, 2003

(54) TREATMENT OF MOVEMENT DISORDERS BY NEAR-DIAPHRAGMATIC NERVE STIMULATION

(75) Inventors: Burke T. Barrett, Houston, TX (US); Reese S. Terry, Jr., Houston, TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 09/917,602

(22) Filed: Jul. 28, 2001

(65) Prior Publication Data

US 2003/0036780 A1 Feb. 20, 2003

(51) Int. Cl.[7] .................................................. A61N 1/00
(52) U.S. Cl. ........................................................ 607/2
(58) Field of Search ................................ 607/2, 45, 48, 607/49, 72

(56) References Cited

U.S. PATENT DOCUMENTS

| | | | |
|---|---|---|---|
| 4,702,254 A | * 10/1987 | Zabara | |
| 4,867,164 A | 9/1989 | Zabara | |
| 5,025,807 A | 6/1991 | Zabara | |
| 5,299,569 A | 4/1994 | Wernicke et al. | |

OTHER PUBLICATIONS

International Search Report mailed Dec. 5, 2002.
Lahmeyer et al., "Biologic Markers in Borderline Personality Disorder: A Review," *J. Clin. Psych.*(1989) 50(6):217–225.
Rush et al., "A Journal of Psychiatric Neuroscience," *Biological Psychiatry*, Feb., 2000.

* cited by examiner

*Primary Examiner*—Scott M. Getzow
(74) *Attorney, Agent, or Firm*—Blank Rome LLP

(57) ABSTRACT

A method for treating patients with movement disorders includes unilaterally or bilaterally stimulating one or both of the left and right branches of a patient's vagus nerve directly or indirectly with an electrical pulse signal generated by an implantable neurostimulator with at least one operatively coupled nerve electrode to apply the pulse signal to the selected nerve branch at a location in the vicinity of the patient's diaphragm, either slightly above or slightly below the diaphragm. A device for performing the method includes a government approved implantable neurostimulator which is programmable to enable physician programming of electrical and timing parameters of the pulse signal, to generate the desired therapy regimen for alleviating the disorder by application of the therapeutic electrical stimulation signal to a selected nerve. Automatic detection or patient sensing of a symptom of the disorder may be utilized for activating the device.

21 Claims, 1 Drawing Sheet

TREATMENT OF MOVEMENT DISORDERS BY NEAR-DIAPHRAGMATIC NERVE STIMULATION

BACKGROUND OF THE INVENTION

The present invention relates generally to methods and apparatus for treating or controlling movement disorders by application of modulating electrical signals to a selected nerve or nerve bundle of the patient, and more particularly to techniques for treating patients with movement disorders by application of such signals to the vagus nerve or other suitable cranial nerve, using an implantable neurostimulator.

It is an object of the present invention to apply the techniques of selective modulation of vagus nerve electrical activity to the treatment of movement disorders, using a neurostimulator device which may be implantable, or used external to the body with only a small portion of the circuitry implanted or with only the nerve electrode(s) and associated lead(s) implanted percutaneously in the body.

In U.S. Pat. Nos. 4,702,254, 4,867,164 and 5,025,807, J. Zabara discloses methods and devices for treating and controlling epileptic seizures and certain motor disorders by selective stimulation of the vagus nerve. The disorders include involuntary movements of the patient during an epileptic seizure, or attributable to Parkinson's disease, palsy or spastic disorders, for example. In the disclosure of the patents, the stimulating electrical pulse signal is preferably applied to the nerve in the patient's neck region. In the '734 patent, movement disorders are also mentioned in connection with discussion of the trigeminal and glossopharngyeal nerves.

In the '254 patent, for example, Zabara discloses methods and devices for performing extra-physiologic electrical stimulation of the vagus nerve for treatment of epilepsy and various forms of involuntary movement disorders. An implantable pulse generator uses neurocybernetic spectral discrimination, in which the external current of the generator is tuned to the electrochemical properties of certain inhibitory nerves that affect the reticular system of the brain. These nerves are embedded within a bundle of other nerves, and are selectively activated directly or indirectly by the tuning of the generator to augment states of brain neural discharge to control convulsions or seizures. The generator may be activated manually by the patient upon recognizing a characteristic of the disorder, such as the classic aura at onset of a seizure, or automatically such as by sensor detection of instantaneous changes in certain state parameters at onset, for treatment only for the duration of the seizure. Alternatively, the generator may be activated for periodic prophylactic treatment.

It is a principal aim of the present invention to provide a new technique for treating movement disorders using stimulation of a suitable cranial nerve, particularly the vagus nerve.

The basic stimulation strategy of the present invention may be implemented by circadian programming to automatically activate the stimulus generator to continuously, periodically or intermittently generate an electrical signal appropriate for application to the patient's vagus nerve to modulate its activity. In another aspect, the treatment is carried out by applying the selectively modulating electrical signals to the patient's vagus nerve in response to the occurrence of a predetermined detectable event.

SUMMARY OF THE INVENTION

According to the present invention, a method of treating patients suffering from involuntary movement disorders, such as but not limited to epileptic seizures, Parkinson's disease, palsy or spastic disorders, comprises unilateral or bilateral stimulation of the left and right vagi in the immediate vicinity of the patient's diaphragm. The treatment is administered at either a supra-diaphragmatic position (i.e., above the diaphragm) or sub-diaphragmatic position (i.e., below the diaphragm) in the ventral cavity. The stimulating electrical signal is preferably applied to the vagus two to three inches above or below the diaphragm, and may be applied either synchronously or asynchronously to both the right and left branches, preferably in the form of a series of pulses applied intermittently to both branches according to a predetermined on/off duty cycle. The intermittent application is preferably chronic, rather than acute. However, continuous application or acute application by bilateral stimulation of the right and left vagi or unilateral stimulation of either branch of the nerve is also contemplated. Automatic delivery of bilateral intermittent stimulation is preferred, but alternatively in the case of certain movement disorders application of the stimulating electrical signal to the right and left vagi may be controlled by an external commencement signal produced by the patient's placement of an external magnet or other signal generating mechanism in proximity to the location of the implanted device.

Preferably, the same stimulating electrical signal is applied to both the right and left vagi, but as an alternative, a stimulating electrical signal might be applied to the right vagus which is different from the stimulating electrical signal applied to the left vagus. And although two separate nerve stimulator generators may be implanted for stimulating the left and right vagi, respectively, as an alternative a single nerve stimulator generator may be implanted for bilateral stimulation if the same signal is to be applied to both the left and right branches of the vagus nerve, whether delivered synchronously or asynchronously to the vagi.

Preferably, the current magnitude of the stimulating signal is programmed to be less than about 6 mA, to be below the retching level of the patient as determined by the implanting physician at the time the implant procedure is performed. This is desirable to avoid patient nausea during periods of vagus nerve stimulation. Preferably, the pulse width is set to a value not exceeding about 500 microseconds ($\mu s$), the pulse repetition frequency is set at about 20–30 Hertz (Hz), the VNS regimen follows alternating periods of stimulation and no stimulation, with the second period about 1.8 to 6 times the length of the first period in the alternating sequence (i.e., the on/off duty cycle is 1:1.8 to 1:6).

Alternative techniques include indirect stimulation of the vagus, either bilaterally or unilaterally, at a location near one or both branches of the nerve or elsewhere, which has the effect of stimulating the vagus nerve as well. This may be accomplished through afferents or efferents, for example. It is also contemplated that direct or indirect unilateral or bilateral stimulation, applied in the vicinity of the patient's diaphragm, of one or more of the other cranial nerves of suitable sensory, motor or mixed fiber types may be effective in treating movement disorders, as an alternative to vagus nerve stimulation.

Some differences may be observed from stimulator to stimulator in magnitude of current in the pulses of the stimulation signal, and may be attributable to things such as patient impedance, variation of the vagus nerve from right to left or between patients, and variation in contact between the vagus and the electrode implanted thereon from implant to implant.

BRIEF DESCRIPTION OF THE DRAWINGS

The above and still further aims, objectives, aspects, features and attendant advantages of the present invention will be better understood from a consideration of the following detailed description of a presently contemplated best mode of practicing the invention, by reference to a preferred exemplary method and embodiment thereof, taken in conjunction with the accompanying Figures of drawing, in which.

DESCRIPTION OF THE PRESENTLY CONTEMPLATED BEST MODE OF PRACTICING THE INVENTION

A generally suitable form of neurostimulator for use in the apparatus and method of the present invention is disclosed, for example, in U.S. Pat. No. 5,154,172 (incorporated herein by reference), assigned to the same assignee as the instant application (the device also referred to from time to time herein as a NeuroCybernetic Prosthesis or NCP device (NCP is a trademark of Cyberonics, Inc. of Houston, Tex., the assignee)). Certain parameters of the electrical stimuli generated by the neurostimulator are programmable, preferably by means of an external programmer (not shown) in a conventional manner for implantable electrical medical devices.

Figure 1:
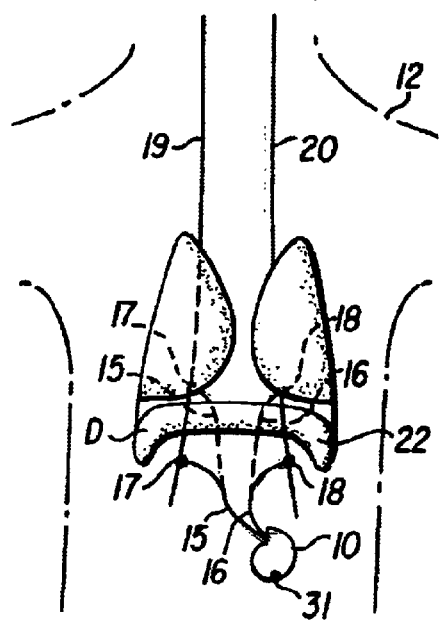
FIG. 1 is a simplified partial front view of a patient (in phantom) having an implanted neurostimulator for generating the desired signal stimuli which are applied directly and bilaterally at a near-diaphragmatic location to the right and left branches of the patient's vagus via an implanted lead/nerve electrode system electrically connected to the neurostimulator.

Referring to FIG. 1, the neurostimulator (sometimes referred to herein as stimulus generator, signal generator, pulse generator, or simply the device), identified in the drawing by reference number 10 is implanted in a patient 12, preferably in the abdominal region, for example, via a left anterior thoracic or laporotomy incision just beneath the skin or outer dermal layer. For the preferred implementation and method of direct bilateral stimulation, lead-electrode pair 15, 16 is also implanted during the procedure, and the proximal end(s) of the lead(s) electrically connected to the neurostimulator. The lead-electrode may be of a standard bipolar lead nerve electrode type available from Cyberonics, Inc.

It will be understood that the overall device generally is required to be approved or sanctioned by government authority for marketing as a medical device implantable in a patient together with electrode means to treat the involuntary movement disorder by stimulation of a selected cranial nerve (e.g., the vagus nerve) of the patient. The treatment is performed using a predetermined sequence of electrical impulses generated by the pulse generator and applied to the selected cranial nerve at a location in a range, preferably, from about two to about three inches above or below the patient's diaphragm, for alleviating symptoms of the movement disorder in the patient. In the United States, the government agency for sanctioning such marketing and use is the U.S. Food and Drug Administration (FDA), while in other countries, sanctioning is typically handled by the counterpart of the FDA for the respective country. Thus, in the United States the same device may not be marketed or used to administer therapy to treat two different diseases or disorders absent FDA approval of the device for both.

According to the preferred method of the invention, the nerve electrodes 17, 18 are implanted on the right and left branches 19, 20, respectively, of the patient's vagus nerve at either a supra-diaphragmatic or sub-diaphragmatic location. The nerve electrodes are equipped with tethers for maintaining each electrode in place without undue stress on the coupling of the electrode onto the nerve itself. Preferably, the location of this coupling is approximately two to three inches above or below the patient's diaphragm 22 for each branch 19, 20.

Neurostimulator 10 generates electrical stimuli in the form of electrical impulses according to a programmed regimen for bilateral stimulation of the right and left branches of the vagus. During the implant procedure, the physician checks the current level of the pulsed signal to ascertain that the current is adjusted to a magnitude at least slightly below the retching threshold of the patient. Typically, if this level is programmed to a value less than approximately 6 mA, the patient does not experience retching attributable to the vagus nerve stimulation (VNS) although variations may be observed from patient to patient. In any event, the maximum amplitude of the current should be adjusted accordingly until an absence of retching is observed, with a suitable safety margin. The retching threshold may change noticeably with time over a course of days after implantation, so the level should be checked especially in the first few days after implantation to determine whether any adjustment is necessary to maintain an effective regimen.

The bilateral stimulation regimen of the VNS preferably employs an intermittent pattern of a period in which a repeating series of pulses is generated for stimulating the nerve, followed by a period in which no pulses are generated. The on/off duty cycle of these alternating periods of stimulation and no stimulation preferably has a ratio in which the off time is approximately 1.8 to 6 times the length of the on time. Nominally, the width of each pulse is set to a value not greater than about 500 $\mu$s, and the pulse repetition frequency is programmed to be in a range of about 20 to 30 Hz. The electrical and timing parameters of the stimulating signal used for VNS as described herein for the preferred embodiment will be understood to be merely exemplary and not as constituting limitations on the scope of the invention.

The intermittent aspect of the bilateral stimulation resides in applying the stimuli according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective in treating movement disorders.

Figure 2:
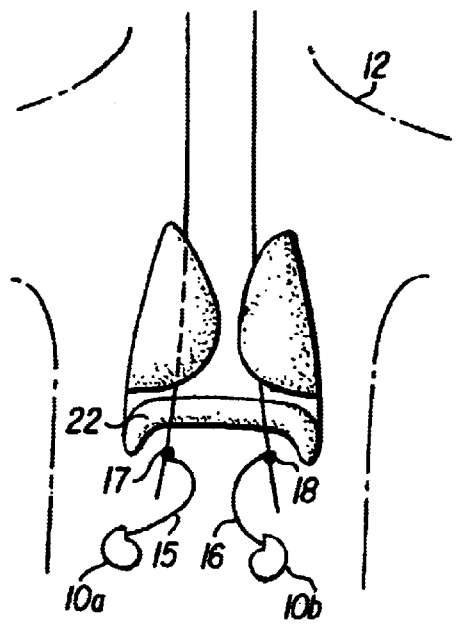
FIG. 2 is a simplified partial front view of a patient similar to that of FIG. 1, but in which a pair of implanted neurostimulators is used for generating the desired signal stimuli.

Also, as shown in FIG. 2, dual implanted NCP devices 10a and 10b may be used as the pulse generators, one supplying the right vagus and the other the left vagus to provide the bilateral stimulation. At least slightly different stimulation for each branch may be effective as well. Use of implanted stimulators for performing the method of the invention is preferred, but treatment may conceivably be administered using external stimulation equipment on an out-patient basis, albeit only somewhat less confining than complete hospitalization.

Implantation of one or more neurostimulators, of course, allows the patient to be completely ambulatory, so that normal daily routine activities including on the job performance is unaffected.

Figure 3:
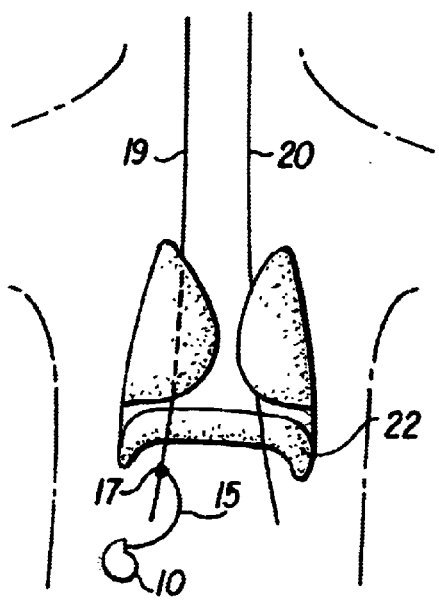
FIG. 3 is a simplified partial front view of a patient in which an implanted neurostimulator and associated electrode is used for unilateral stimulation of only one branch of the vagus nerve at the near-diaphragmatic location.

The desired stimulation of the patient's vagus nerve may also be achieved by performing unilateral supra-diaphragmatic or sub-diaphragmatic stimulation of either the left branch or the right branch of the vagus nerve, as shown in FIG. 3. A single neurostimulator 10 is implanted together with a lead 15 and associated nerve electrode 17. The nerve electrode 17 is implanted on either the right branch 19 or the left branch 20 of the nerve, preferably in a location in a range of from about two to about three inches above or below the patient's diaphragm 22. The electrical signal stimuli are the same as described above.

Figure 4:
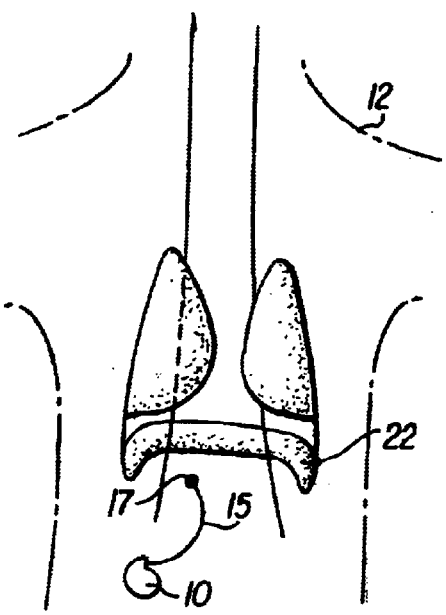
FIG. 4 is a simplified partial front view of a patient in which the signal stimuli are applied at a portion of the nervous system remote from the vagus nerve, for indirect stimulation of the vagus nerve at the near-diaphragmatic location.

In a technique illustrated in FIG. 4, the signal stimuli are applied at a portion of the nervous system remote from the vagus nerve, for indirect stimulation of the vagus nerve in the vicinity of the diaphragmatic location. Here, at least one signal generator 10 is implanted together with one or more electrodes 17 subsequently operatively coupled to the generator via lead 15 for generating and applying the electrical signal internally to a portion of the patient's nervous system other than the vagus nerve, to provide indirect stimulation of the vagus nerve in the vicinity of the desired location. Alternatively, the electrical signal stimulus may be applied non-invasively to a portion of the patient's nervous system for indirect stimulation of the vagus nerve at the near-diaphragmatic location.

In treating the disorder, detection strategies such as sensing patient movement, particularly of the extremities, which appears to be random, uncoordinated and involuntary, may be employed to trigger the stimulation. To that end, a small accelerometer 30 in its own case may be separately implanted such as in a leg or arm of the patient to detect such movement. Or instead, the accelerometer may be mounted integrally in the same case that houses the neurostimulator. Alternatively, the vagal stimulation may be performed without need for detection of a symptom characteristic of the disorder or onset of the disorder. In that case, the stimulation is continuous, or it may be periodic, or intermittent during prescribed segments of the patient's circadian cycle. For example, stimulation may be periodic with a random frequency for the stimulating pulse waveform. In any event, this regimen of vagal stimulation is programmed into the neurostimulator device 10 (or 10a, 10b, as the case may be).

Since the patient is generally able to quickly recognize the symptoms of the movement disorder, where it is characterized by sudden onset or other random condition, provision may be made and preferably is made for patient activation of the neurostimulator for treatment of the particular movement disorder. For example, certain techniques of manual and automatic activation of implantable medical devices are disclosed in U.S. Pat. No. 5,304,206 to R. G. Baker, Jr. et al. (referred to herein as "the '206 patent"), which is assigned to the same assignee as the present application. According to the '206 patent, means for manually activating or deactivating the stimulus generator may include a sensor such as a piezoelectric element 31 mounted to the inner surface of the generator case and adapted to detect light taps by the patient on the implant site. One or more taps applied in fast sequence to the skin above the location of the stimulus generator in the patient's body may be programmed into the device as the signal for activation of the generator, whereas two taps spaced apart by a slightly longer time gap is programmed as the signal for deactivation, for example. The therapy regimen performed by the implanted device(s) remains that which has been pre-programmed by means of the external programmer, according to the prescription of the patient's physician in concert with recommended programming techniques provided by the device manufacturer. In this way, the patient is given limited but convenient control over the device operation, to an extent which is determined by the program dictated and/or entered by the attending physician.

Where sense electrodes are to be utilized to detect onset of the movement disorder being treated, a signal analysis circuit is incorporated in the neurostimulator. Upon detection of the symptom of interest of the disorder being treated, the processed digital signal is supplied to a microprocessor in the neurostimulator device, to trigger application of the stimulating signal to the patient's vagus nerve.

The principles of the invention may be applicable to selected cranial nerves other than the vagus nerve, to achieve the desired results. Hence, although certain preferred methods and modes of treating and controlling movement disorders through a regimen generally of cranial nerve, and specifically vagus nerve stimulation directly or indirectly at a near-diaphragmatic location have been described herein, it will be appreciated by persons of ordinary skill in the art of nerve stimulation for treatment of diseases and disorders that variations and modifications may be made within the scope of the present invention as defined by the appended claims. It is therefore intended that the invention shall be limited only as required by the appended claims and by the rules of applicable law.

What is claimed is:

1. A method of treating patients suffering from a movement disorder, which comprises the step of stimulating a patient's vagus nerve with an electrical pulse signal applied directly or indirectly thereto at a location in the immediate vicinity of the patient's diaphragm, including selectively programming electrical and timing parameters of said electrical pulse signal according to a predetermined therapy regimen for alleviating the disorder.

2. The method of claim 1, wherein the step of stimulating the patient's vagus nerve comprises performing unilateral supra- or sub-diaphragmatic stimulation of either the left branch or the right branch of the vagus nerve.

3. The method of claim 1, wherein the step of stimulating the patient's vagus nerve comprises performing bilateral supra- or sub-diaphragmatic stimulation of the left and right branches of the vagus nerve.

4. The method of claim 1, including implanting at least one signal generator and electrodes operatively coupled thereto for generating and applying said electrical signal to the vagus nerve at said location.

5. The method of claim 1, including implanting at least one signal generator and electrodes operatively coupled thereto for generating and applying said electrical signal internally to a portion of the patient's nervous system other than the vagus nerve to indirectly stimulate the vagus nerve at said location.

6. The method of claim 1, wherein said stimulating electrical signal comprises a sequence of electrical pulses.

7. The method of claim 1, wherein the step of stimulating comprises applying said electrical signal to the vagus nerve at a location in a range of from about two to about three inches above or below the patient's diaphragm.

8. The method of claim 1, wherein the step of stimulating comprises applying said electrical signal intermittently, in alternating on and off intervals according to a predetermined duty cycle.

9. The method of claim 1, wherein the step of stimulating comprises applying said electrical signal continuously.

10. The method of claim 1, wherein the step of stimulating comprises applying said electrical signal according to the patient's circadian rhythm.

11. The method of claim 1, wherein the step of stimulating comprises applying said electrical signal bilaterally and synchronously to both branches of the vagus nerve.

12. The method of claim 1, wherein the step of stimulating comprises applying said electrical signal non-invasively to a portion of the patient's nervous system other than the vagus nerve to indirectly stimulate the vagus nerve at said location.

13. The method of claim 1, including detecting random, uncoordinated involuntary movement of the patient characteristic of the disorder, and thereupon triggering application of said stimulating electrical pulse signal to the vagus nerve at said location.

14. The method of claim 1, including programming for initiation of the electrical stimulation by the patient upon sensing a symptom characteristic of onset of the disorder, to trigger application of said stimulating electrical pulse signal to the vagus nerve at said location.

15. A method of treating patients suffering from involuntary movement disorders by stimulating a selected cranial nerve of the patient with an electrical signal applied to induce a signal up the nerve toward the brain from a location in the vicinity of the patient's diaphragm, including programming electrical and timing parameters of said electrical signal to ameliorate said disorder.

16. The method of claim 15, including applying said electrical signal directly to the selected cranial nerve at a location substantially immediately above or below the diaphragm.

17. The method of claim 15, including applying said electrical signal internally to a portion of the patient's nervous system remote from the selected cranial nerve to indirectly stimulate the selected cranial nerve at said location.

18. The method of claim 15, wherein said stimulating electrical signal comprises a sequence of electrical pulses.

19. The method of claim 15, wherein the step of stimulating comprises applying said electrical signal to the selected cranial nerve at said location in a range of from about two to about three inches above or below the patient's diaphragm.

20. The method of claim 15, including detecting involuntary movement of the patient characteristic of the disorder, and thereupon triggering application of said stimulating electrical signal to the selected cranial nerve at said location.

21. The method of claim 15, including programming for initiation of the stimulating electrical signal by the patient upon sensing a symptom characteristic of onset of the movement disorder, to trigger application of said stimulating electrical pulse signal to the selected cranial nerve at said location.

* * * * *